US010905696B2

(12) United States Patent
Trogden et al.

(10) Patent No.: US 10,905,696 B2
(45) Date of Patent: *Feb. 2, 2021

(54) ANDROGEN COMPOSITION FOR TREATING AN OPHTHALMIC CONDITION

(71) Applicant: Allergan, Inc., Irvine, CA (US)

(72) Inventors: John T. Trogden, Anaheim, CA (US); Adnan K. Salameh, Irvine, CA (US); Chetan P. Pujara, Irvine, CA (US); Anuradha V. Gore, Irvine, CA (US); Jaya Giyanani, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/362,032

(22) Filed: Nov. 28, 2016

(65) Prior Publication Data

US 2017/0189412 A1 Jul. 6, 2017

Related U.S. Application Data

(63) Continuation of application No. 14/840,276, filed on Aug. 31, 2015, now Pat. No. 9,504,646, which is a continuation of application No. 13/357,779, filed on Jan. 25, 2012, now Pat. No. 9,119,772.

(60) Provisional application No. 61/436,274, filed on Jan. 26, 2011.

(51) Int. Cl.
*A61K 31/568* (2006.01)
*A61K 9/00* (2006.01)
*A61K 9/107* (2006.01)
*A61K 47/44* (2017.01)
*A61K 45/06* (2006.01)
*A61K 47/32* (2006.01)
*A61K 47/26* (2006.01)
*A61K 47/02* (2006.01)
*A61K 47/10* (2017.01)
*A61K 47/06* (2006.01)
*A61K 31/5685* (2006.01)
*A61K 31/569* (2006.01)
*A61K 47/40* (2006.01)

(52) U.S. Cl.
CPC .............. *A61K 31/568* (2013.01); *A61K 9/00* (2013.01); *A61K 9/0048* (2013.01); *A61K 9/107* (2013.01); *A61K 31/569* (2013.01); *A61K 31/5685* (2013.01); *A61K 45/06* (2013.01); *A61K 47/02* (2013.01); *A61K 47/06* (2013.01); *A61K 47/10* (2013.01); *A61K 47/26* (2013.01); *A61K 47/32* (2013.01); *A61K 47/40* (2013.01); *A61K 47/44* (2013.01)

(58) Field of Classification Search
None
See application file for complete search history.

(56) References Cited

U.S. PATENT DOCUMENTS

| | | |
|---|---|---|
| 2,262,182 A | 11/1941 | Huskamp |
| 5,134,127 A | 7/1992 | Stella et al. |
| 5,364,632 A | 11/1994 | Benita et al. |
| 5,376,645 A | 12/1994 | Stella et al. |
| 5,474,979 A | 12/1995 | Ding et al. |
| 5,620,921 A | 4/1997 | Sullivan |
| 5,958,912 A | 9/1999 | Sullivan |
| 5,981,607 A | 11/1999 | Ding et al. |
| 6,093,706 A | 7/2000 | Zeligs |
| 6,107,289 A | 8/2000 | Sullivan |
| 6,114,319 A | 9/2000 | Kimura et al. |
| 6,429,227 B1 | 8/2002 | Schneider et al. |
| 7,629,331 B2 | 12/2009 | Pipkin et al. |
| 7,635,773 B2 | 12/2009 | Antle |
| 8,049,003 B2 | 11/2011 | Mosher et al. |
| 2002/0009507 A1* | 1/2002 | Weimer ............... A61K 9/0048 424/731 |
| 2003/0109508 A1 | 6/2003 | Yanni et al. |
| 2003/0144635 A1 | 7/2003 | Connor |
| 2004/0214797 A1 | 10/2004 | Lyons et al. |
| 2006/0210645 A1 | 9/2006 | Du Mee et al. |
| 2007/0248645 A1 | 10/2007 | Bague et al. |
| 2008/0045486 A1* | 2/2008 | Tang-Liu ............... A61K 31/57 514/170 |
| 2008/0045846 A1 | 2/2008 | Friedman et al. |
| 2009/0092612 A1 | 4/2009 | Takayama et al. |
| 2010/0305046 A1* | 12/2010 | Yu ........................ A61K 9/0048 514/20.5 |

FOREIGN PATENT DOCUMENTS

| | | |
|---|---|---|
| DE | 3514724 A1 | 10/1986 |
| EP | 2667877 | 8/2012 |
| WO | 1994020598 A1 | 9/1994 |
| WO | 2006094026 A1 | 9/2006 |
| WO | 2008070728 A2 | 6/2008 |

(Continued)

OTHER PUBLICATIONS

Khanal et al. in Cornea 26(2), 175-181 (2007) (Year: 2007).*
John et al. in Ann. Ophthalmol. 40(2), 68-74 (2008) (Year: 2008).*
Natalonie, R, in Ocular Surgery News U.S. Edition, Jun. 15, 2001 (retrieved from the internet, Apr. 9, 2019) (Year: 2001).*
"Dry Eye" in http:/emedicine.medscape.com/article/1210417-overview.
A Single-Center, Double-Masked, Randomized, Vehicle Controlled Study to Evaluate the Safety and Efficacy of Testosterone 0.03% Ophthalmic Solution Compared to Vehicle for the Treatment of Meibomian Gland Dysfunction, Internet, Sep. 17, 2008, https://clinicaltrials.gov/ct2/show/study/NCT00755183.

(Continued)

Primary Examiner — Dennis Heyer
(74) Attorney, Agent, or Firm — Lorenz Siddiqi

(57) ABSTRACT

The disclosure provides compositions for treating an ocular condition. The composition comprises a physiologically effective amount of an androgen, wherein the composition is suitable for topical administration to an eye. The disclosure further provides methods for treating an ocular condition with the disclosed compositions.

28 Claims, No Drawings

(56) References Cited

FOREIGN PATENT DOCUMENTS

| | | |
|---|---|---|
| WO | 2008070728 A3 | 8/2008 |
| WO | 2012103186 A3 | 9/2012 |

OTHER PUBLICATIONS

Abelson, Mark et al, Demstifying Dumulcents, Review of Ophthalmology, 2006, 4 Pages.

Afshari, Research in cornea and external disease in refining current concept and branching out into new avenues of investigation, Rev Ophthalmol Online, 2006, 11 pages, 5 (13), US.

Avunduk, A.M., et al., The Comparison of Efficacies of Topical Corticosteroids and Nonsteroidal Anti-inflammatory Drops on Dry Eye Patients: A Clinical and Immunocytochemical Study, American Journal of Ophthalmology, Oct. 2003, 593-602, 136, Elsevier Inc.

Babar, A. et al, Diadermatic Dose Forms of Testosterone: In-Vitro Release Studies and In-Vivo Absorption in a Human Male, Drug Development and Industrial Pharmacy, 1989, 1405-1422, 15(9).

Bonina, F. et al, Three Phase Emulsions for Controlled Delivery in the Cosmetic Field, International Journal of Cosmetic Science, 1992, 65-74, 14.

Danner, CH. et al, Androgen Substitution with Testosterone Containing Nasal Drops, International Journal of Andrology, 1980, 429-435, 3.

Donnenfeld, Eric et al, Topical Ophthalmic Cyclosporine: Pharmacology and Clinical Uses, Survey of Ophthalmology, Jun. 2009, 321-338, 54(3).

El-Kamel, Amal et al, Testosterone Solid Lipid Microparticles for Transdermal Drug Delivery. Formulation and Physicochemical Characterization, Journal of Microencapsulation, 2007, 457-475, 24(5).

Foster, Stephen, Dry Eye Syndrome, Dec. 2013, 1 Page, Retrieved from http://emedicine.medscape.com/article/1210417—overview on Mar. 7, 2014.

http://en.wikipedia.org/wiki/Propylene_glycol (Retrieved from the internet Oct. 9, 2014).

http://msdssearch.dow.com/PublishedLiteratureDOWCOM/dh_006e/0901b8038006e13c.pdf?filepath=propyleneglycol/pdfs/noreg/117-01785.pdf&fromPage=GetDCoc (Retrieve from the internet Oct. 9, 2014).

Johnson, Michael et al, Changes in the Tear Film and Ocular Surface From Dry Eye Syndrome, Progess in Retinal and Eye Research, 2004, 449-474, 23.

Khanal, Santoush, et al., Effect of an Oil-in-Water Emulsion on the Tear Physiology of Patients with Mild to Moderate Dry Eye, Cornea, Feb. 2007, 175-181, vol. 26, No. 2, Lippincott Williams & Wilkins.

Knop, Erich et al, The International Workshop on Meibomian Gland Dysfunction: Report of the Subcommittee on Anatomy, Physiology, and Pathophysiology of the Meibomian Gland, IOVS, 2011, 1938-1978, 52(4).

Ko, Kuang-Ta et al, Emulsion Formulations of Testosterone for Nasal Administration, J. Microencapsulation, 1998, 197-205, 15(2).

Loftsson, T. et al, Cyclodextrins as Co-Enhancers in Dermal and Transdermal Drug Delivery, Pharmazie, 1998, 137-139, 53.

Messmer, E.M., Management of Keratoconjunctivitis Sicca in Sjogren's Syndrome, Aktuelle Rheumatologie, 2005, 59-65, 30(1).

Neiberg, Maryke et al, Phlyctenular Keratoconjunctivitis in a Patient with Staphylococcal Blepharitis and Ocular Rosacea, Optometry, 2008, 133-137, 79.

Notification of Transmittal of the International Search Report and the Written Opinion of the International Searching Authority, or the Declaration, International Application No. PCT/US2012/025508, International Filing Date Jan. 25, 2012, dated Aug. 9, 2012.

Santosh Khanal, et al., Effect of an Oil-In-Water Emulsion on the Tear Physiology of Patients With Mild to Moderate Dry Eye, Cornea, Feb. 2007, 175-181, 26 (2), US.

Schiffman, R.M., et al., A Multi-Center, Double-Masked, Randomized, Vehicle-Controlled, Parallel Group Study to Evaluate the Safety and Efficacy of Testosterone Ophthalmic Solution in Patients With Meibomian Gland Dysfunction, Investigative Ophthalmology & Visual Science, May 2006, 5608, vol. 47, No. 13, Association for Research in Vision and Ophthalmology.

Schroeder, Ines Zurdo et al, Development and Characterization of Flim Forming Polymeric Solutions for Skin Drug Delivery, European Journal of Pharmaceutics and Biopharmaceutics, 2007, 111-121, 65.

Tsubuku, Satoru et al, Preparation and Characterization of Oil-in-Water Type Poly (D,L-Lactic Acid) Microspheres Containing Testosterone Enanthate, Drug Development and Industrial Pharmacy, 1998, 927-934, 24(10).

"Safety and Efficacy Study of a Testosterone Eye Drop forthe Treatment of Meibomian Gland Dysfunction" (§)https://clinicaltrials.gov/ct2/show/NCT00755183? term=NCT00755183&rank=1.

Bryne, J., Dry eye treatment: a growing priority in the future of optometry, Primary Care Optometry News, 2004, 10 pgs.

Glenn, C., New Thinking Spurs New Products, Rev. Ophthalmol., 2003, 5 pgs.

John, T., et al., Use of azithromycin ophthalmic solution in the treatment of chronic mixed anterior blepharitis, Annals Ophthalmology, 2008, 68-74, 40 (2).

\* cited by examiner

ANDROGEN COMPOSITION FOR TREATING AN OPHTHALMIC CONDITION

CROSS-REFERENCE TO RELATED APPLICATION

This application is a continuation of copending U.S. patent application Ser. No. 14/840,276, filed on Aug. 31, 2015, which is a continuation of U.S. patent application Ser. No. 13/357,779, filed on Jan. 25, 2012, which claims the benefit of U.S. Provisional Patent Application No. 61/436,274 filed on Jan. 26, 2011, the entirety of both applications are incorporated herein by reference.

BACKGROUND

Blepharitis is a disorder of the meibomian glands, which produce the lipid component of tear film. Both the upper and lower eye lids contain 30-40 glands, located beneath the skin. The glandular pores open just behind the base of the eye lashes on the eye lid margin. With blepharitis, the glands become inflamed and the pores become blocked. Symptoms of blepharitis include eye irritation, soreness, redness and an accumulation of matter on the eyelids. Patients may also experience dry eye as well. As a result of these symptoms, blepharitis is commonly misdiagnosed as conjunctivitis or dry eye.

In certain cases, a local androgen deficiency can cause blepharitis. Topical compositions containing an androgen would be desirable for the treatment of blepharitis.

BRIEF SUMMARY

The disclosure provides compositions and methods for treating one or more ocular conditions.

In one embodiment, a composition is provided comprising a physiologically effective amount of an androgen, wherein said composition is suitable for topical administration to an eye.

In another embodiment, a method for treating an ocular condition resulting from an androgen deficiency is disclosed. The method comprises administering an effective amount of an ophthalmic composition comprising a physiologically effective amount of an androgen, wherein said composition is suitable for topical administration to an eye, and wherein at least one symptom of the ocular condition is alleviated.

DETAILED DESCRIPTION

The disclosure provides an ophthalmic composition comprising a physiologically effective amount of an androgen, wherein said composition is suitable for topical administration to an eye.

A method for treating an ocular condition associated with an androgen deficiency is also disclosed herein. The method comprises administering an effective amount of an ophthalmic composition comprising a physiologically effective amount of an androgen, wherein said composition is suitable for topical administration to an eye, and wherein at least one symptom of the ocular condition is alleviated.

The compositions disclosed herein comprise an androgen. As used herein, unless otherwise specified, the term "androgen" includes all testosterone and testosterone containing moieties, endogenous and synthetic, as well as isomers, analogues, esters, and combinations thereof. The androgen can be an endogenously produced steroidal androgen, which includes, but is not limited to, testosterone (i.e., (17β)-17-hydroxyandrost-4-ene-3-one), dihydrotestosterone (DHT), dehydroepiandrosterone, androstenedione, androstenediol, and androsterone. Further included are testosterone-containing moieties, for example, esters of testosterone, such as the cypionate, propionate, phenylpropionate; cyclopentylpropionate, isocaproate, enanthate, phenylacetate, acetate, buciclate, heptanoate, caprate, isocaprate, and decanoate esters, and other synthetic androgens such as oxymetholone, 17α-methylnortestosterone, and 7-methylnortestosterone and its acetate ester.

The ocular condition can be any condition of an eye, eye lid, gland, or skin surrounding the eye resulting from a local or systemic androgen deficiency. In certain embodiments, the ocular condition is blepharitis. Androgen deficiency can occur for a variety of reasons, for instance, during menopause or as a result of the natural aging process. Androgen deficiency can be due to a disease or condition, such as Sjögren's syndrome.

The patient to be treated can be any mammal of any age, or gender. The mammal can be a human, dog, cat, sheep, cow, etc. in need of treatment. In certain embodiments, the patient to be treated is a human, male or female.

A physiologically effective amount refers to an amount of a substance that is sufficient to achieve the intended purpose or effect. Various biological factors can influence the amount required to be effective, for instance, age, gender, severity of the underlying condition, and overall health of the patient. As used herein, a dosage is considered effective if it prevents, reduces, or eliminates the symptoms associated with the ocular condition to be treated.

The androgen can be present in the ophthalmic compositions described herein in an amount of about 0.001% to about 5% by weight (w/w), or from about 0.09% to about 2% by weight, or from about 0.01% to about 1.0% (w/w).

The disclosed compositions can be emulsions, solutions, suspensions, gels, ointments, occlusive films, or a sustained release films and they can be preserved or non-preserved formulations. The compositions can be formulated as eye drops, creams, ointments, and films that can be applied to an eye. The formulations can be administered to the eye, the upper eye lid, the lower eye lid, or a combination thereof. Topical administration of the compositions provides treatment at the site of the condition with minimal systemic levels of the medicament.

Listed in Table 1 are examples of formulation ingredients and exemplary concentrations.

TABLE 1

| Function | Ingredient | Composition (% w/w) |
|---|---|---|
| Active | testosterone | 0.01-1.0 |
| Thickener | carbomer, sodium carboxymethylcellulose, methylcellulose, hydroxypropyl methylcellulose, polyvinyl alcohol, zanthan gum | 0-3.0 |
| Neutralizing Agent | sodium hydroxide, organic bases | 0-2.0 |
| Emulsifier | polysorbate 20, polysorbate 40, polysorbate 60, polysorbate 80, POE-40-stearate, Pemulen ® and other polymeric emulsifiers. | 0-2.0 |
| Lipophilic Vehicle | castor oil, squalane, isostearyl isostearate, isopropyl myristate, , mineral oil, silicone oil, caprylic/capric triglycerides, cetyl alcohols, stearyl alcohols | 0-80 |

TABLE 1-continued

| Function | Ingredient | Composition (% w/w) |
|---|---|---|
| Co-solvents | diethylene glycol monoethyl ether, propylene glycol, dipropylene glycol dimethyl ether, diethylene glycol, dipropylene glycol | 0-80 |
| Buffering Agent | sodium citrate dihydrate, boric acid, monosodium phosphate, monohydrate, sodium phosphate dibasic heptahydrate, sodium phosphate monobasic monohydrate | 0-2 |
| Tonicity Agent | Glycerin, erythritol, mannitol, potassium chloride, sodium chloride, | 0-3 |
| Solubilizer | Cyclodextin, alpha-cyclodextrin, beta-cyclodextrin, gamma-cyclodextrin, hydroxypropyl-beta-cyclodextrin, Sulfobutyl ether-β-cyclodextrin (Captisol ®) | 0-10 |
| Demulcent | carboxymethylcellulose sodium, hydroxypropyl methylcellulose hydroxyethyl cellulose, methylcellulose, polyvinyl alcohol, povidone, glycerin, propylene glycol, PEG 300, PEG 400 | 0-10 |
| Preservative | benzalkonium chloride, PURITE ®, and other ophthalmic preservatives | 0-2.0 |
| Plasticizer | Silicone oils, isostearyl alcohol, cetyl alcohol, glycerin | 0-5.0 |
| Occlusive Agent | silicone oils, petrolatum, waxes | 0-80 |
| Film Former | acrylate/octylacrylamide copolymer, poly(ethyl acrylate, methyl methacrylate), chitosan, polyvinyl alcohol, polyisobutylene, polyvinylpyrrolidone-vinyl acetate copolymer, silicon gum, polyvinylpyrrolidone, other sustained release polymeric films | 0-10 |
| Hydrophilic Vehicle | water | 0-99 |

The emulsions of the disclosed compositions can be stabilized using one or more polyelectrolytes from the family of cross-linked polyacrylates, such as carbomers and PEMULEN® (Lubrizol). Pemulens are high molecular weight co-polymers of acrylic acid and a long chain alkyl methacrylate cross-linked with allyl ethers of pentaerythritol. They contain not less than about 52% and not more than about 62% of carboxylic acid groups. The viscosity of a neutralized 1.0% aqueous dispersion is between about 9,500 and about 26,500 centipoise. Additional emulsifiers include, but are not limited to, polysorbate-80, POE-40-Stearate, polysorbate-20, polysorbate 40, polysorbate-60, and a combination thereof in an amount of about 0% to about 4% or about 0.01 to about 2.0% by weight of the composition.

In some embodiments, the composition comprises a lipophilic vehicle such as, for example, castor oil, squalane, diethylene glycol monoethyl ether, propylene glycol, isostearyl isostearate, isopropyl myristate, dipropylene glycol dimethyl ether, diethylene glycol, dipropylene glycol, mineral oil, silicone oil, caprylic/capric triglycerides, cetyl alcohols, stearyl alcohols, and a combination thereof. The lipophilic vehicle can be present in an amount of about 0% to about 85%, or about 1% to about 50%, or about 2% to about 15% of the composition by weight.

The disclosed compositions can comprise a neutralizing agent such as sodium hydroxide and organic bases in an amount of about 0 to about 2.5% by weight of the composition.

In certain embodiments, the composition may include a demulcent such as carboxymethylcellulose sodium, hydroxypropyl methylcellulose, hydroxyethyl cellulose, methylcellulose, polyvinyl alcohol, povidone, glycerin, propylene glycol, PEG 300, PEG 400, and a combination thereof. The demulcent can be present in an amount of about 0 to about 10%, or about 2%, 5%, 7%, or 9%, by weight of the composition.

In some embodiments, the composition comprises a tonicity agent such as sodium chloride, glycerin, mannitol, potassium chloride, erythritol, and a combination thereof, in an amount of about 0 to about 4% or about 0.01% to about 3% by weight of the composition.

In some embodiments, the composition may include one or more buffering agents. Suitable buffering agents include, but are not limited to, phosphates, citrates, acetates, borates, and combinations thereof. The amount of buffer component employed is sufficient to maintain the pH of the composition in a range of about 6 to about 8, or from about 6.5 to about 7.5. In certain embodiments, the buffer is present in an amount of about 0 to about 2.0% by weight of the composition.

In certain embodiments, the composition includes a thickener or viscosity agent. The viscosity agent can be selected from the group consisting of carbomer, sodium carboxymethyl cellulose, methyl cellulose, hydroxypropyl methyl cellulose, polyvinyl alcohol, xanthan gum, and a combination thereof. The viscosity agent can be present in an amount of about 0% to about 4% or about 0.01% to about 3.0% by weight of the composition.

In certain embodiments, the composition includes a solubilizer or solubility enhancing agent. The solubilizer or solubility enhancing agent can be selected from the group consisting of Cyclodextrin, alpha-cyclodextrin, beta-cyclodextrin, gamma-cyclodextrin, hydroxypropyl-beta-cyclodextrin, Sulfobutyl ether-β-cyclodextrin (Captisol®) and a combination thereof. The solubilizer or solubility enhancing agent can be present in an amount of about 0% to about 10%. In some embodiments; the solubilizer or solubility enhancing agent can be present in an amount of about 0.01% to about 7.0%. In some embodiments; the solubilizer or solubility enhancing agent can be present in an amount of about 0.1 to about 4% by weight of the composition.

The composition can be administered topically in the form of a solution (i.e., drops), cream, ointment, film, or the like. The composition can be administered to a left eye, a right eye, or both eyes. When the composition is administered as a solution, a drop of solution should disperse readily upon contact with a tear solution.

The compositions of, or used in, the present disclosure may include one or more other components in amounts effective to provide one or more useful properties and/or benefits. For example, although the present compositions may be substantially free of added preservative components, in other embodiments, the present compositions include effective amounts of preservative components. Examples of such preservative components include, without limitation, PURITE® (Allergen, Irvine, Calif.), quaternary ammonium preservatives such as benzalkonium chloride ("BAC" or "BAK") and poloxamer; biguanidebiguanide preservatives such as polyhexamethylene biguanidebiguanide (PHMB); methyl and ethyl parabens; hexetidine; chlorite components, such as stabilized chlorine dioxide, metal chlorites and the like; other ophthalmically acceptable preservatives and mixtures thereof. The concentration of the preservative component, if any, in the present compositions is a concentration effective to preserve the composition, and (depending on the nature of the particular preservative used) is often and generally used in a range of about 0% to about 4.0% by volume or about 0.1% to about 2.0% by volume of the composition, In certain embodiments, the composition can be in the form of a film, such as an occlusive film or a sustained release film. Also contemplate dare liquids that dry to form films. Where films are employed, the films will be in the range of at least about 0.5 mm×0.5 mm, usually about 3-10 mm×5-10 mm with a thickness of about 0.1-1.0 mm for ease of handling. The size and form of the film can be used to control the rate of release. Such compositions can comprise one or more film forming agents such as acrylate/octylacrylamide copolymer, poly(ethyl acrylate, methyl methacrylate), chitosan, polyvinyl alcohol, polyisobutylene, polyvinylpyrrolidone-vinyl acetate copolymer, silicon gum, polyvinylpyrrolidone, other sustained release polymeric films, and a combination thereof. The film forming agent can be present in an amount of about 0% to about 10% by weight of the composition.

The frequency, duration, and dosage of the administration are determined by the prescribing physician. The dosage can vary depending on the dosage form. When the composition is a solution, for example, 1, 2, 3, or more drops can be administered per eye per administration. Frequency of administration can be one or more times daily (such as once, twice, three, or four or more times daily), bi-weekly, and/or monthly. Duration of administration can continue until the condition to be treated is resolved, that is, until one or more symptoms of the ocular condition are reduced or eliminated. Accordingly, the composition can be administered for hours, days, weeks, months, and years.

A symptom is considered to be alleviated if it is prevented, reduced or eliminated. A symptom is prevented in a patient that typically experiences a particular symptom with the ocular condition (or if patients similarly situated typically experience a particular symptom) and the patient does not experience the onset of the symptom following administration of the disclosed composition. A reduction of a symptom is considered achieved if there is a 5%, 10%, 20%, 50%, 75%, 90% or more reduction in the severity or duration of one or more symptom associated with the ocular condition, in a patient. An elimination of one or more symptoms associated with the ocular condition is achieved when it ceases to be present or substantially present in a patient.

Certain embodiments of the disclosed compositions incorporate a local anesthetic, which can be selected from the group of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, fomocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof. The concentration of the local anesthetic in the compositions described herein can be therapeutically effective, meaning the concentration is adequate to provide a therapeutic benefit without inflicting harm to the patient.

The compositions can further comprise an ophthalmologically acceptable anti-inflammatory agent, such as any non-steroidal anti-inflammatory drug (NSAD) in an amount effective, to reduce inflammation in an eye. Non-limiting examples include agents that inhibit the cyclooxygenase (COX)-1 and/or -2 enzyme, including but not limited to propionic acids such as naproxen, flurbiprofen, oxaprozin, ibuprofen, ketoprofen, fenoprofen; ketorolac tromethamine; acetic acid derivatives such as sulindac, indomethacin, and etodolac; phenylacetic acids such as diclofenac, bromfenac, and suprofen; arylacetic prodrugs such as nepafenac, and amfenac; salicylic acids, such as aspirin; salsalate, diflunisal, choline magnesium trisalicylate (CMT); para-aminophenol derivatives such as acetaminophen; naphthylalkanones such as nabumetone; enolic acid derivatives such as piroxicam and meloxicam; femanates such as mefenamic acid, meclofenamate and flufenamic acid; pyrroleacetic acids such as tolmetin; and pyrazolones such as phenylbutazone; COX-2 selective inhibitors such as celecoxib, valdecoxib, parecoxib, etoricoxib, and lumiracoxib; including all esters and pharmaceutically acceptable salts thereof. A steroidal anti-inflammatory agent can also be incorporated, in certain embodiments, and can include, without limitation, hydrocortisone, cortisone, prednisolone, and prednisone.

Antimicrobial agents suitable for use in the disclosed compositions include, but are not limited to, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxacillin, methicillin; lincosamides such as lincomycin; polypeptide antibiotics such as polymyxin and bacitracin; tetracyclines such as tetracycline; quinolones such as ciprofloxacin, etc.; sulfonamides such as chloramine T; and sulfones such as sulfanilic acid as the hydrophilic entity; as well as anti-viral drugs, e.g. acyclovir, gancyclovir, ganciclovir, vidarabine, azidothymidine, dideoxyinosine, and dideoxycytosine. Antifungal agents and any other ophthalmically suitable antimicrobials are contemplated herein as well.

Tables 2, 3, and 4 provide non-limiting exemplary eye drop, cream, and film formulations, respectively.

TABLE 2

| Ingredient | Function | % w/w |
|---|---|---|
| testosterone | active | 0.03 |
| castor oil | lipophilic vehicle | 2.0 |
| Pemulen TR-1 | emulsifier | 0.15 |
| polysorbate 80 | emulsifier | 0.1 |
| sodium hydroxide | neutralizing Agent | QS pH 7.3 |
| Glycerin | demulcent/tonicty agent | 1.0 |
| mannitol | tonicity | 2.0 |
| PURITE ® | preservative | 0.01 |
| Water | hydrophilic vehicle | QS 100 |

TABLE 3

| Ingredient | Function | % w/w |
|---|---|---|
| testosterone | active | 0.05 |
| squalane | lipophilic vehicle | 12.0 |
| diethylene glycol monoethyl ether | lipophilic vehicle | 3.0 |
| Pemulen TR-1 | emulsifier | 0.1 |
| Polsorbate 80 | emulsifier | 0.1 |
| Carbomer | thickener | 0.1 |
| Sodium hydroxide | neutralizing Agent | QS pH 6.5 |
| PURITE ® | preservative | 0.01 |
| Water | hydrophilic vehicle | QS 100 |

TABLE 4

| Ingredient | Function | % w/w |
|---|---|---|
| testosterone | active | 0.05 |
| squalane | lipophilic vehicle | 10 |
| diethylene glycol monoethyl ether | lipophilic vehicle | 10 |
| Pemulen TR-2 | emulsifier | 0.2 |
| Glycerin | plasticizer | 4.0 |
| Isostearyl alcohol | plasticizer | 1.0 |
| acrylate/octylacrylamide copolymer | film former | 2.5 |
| Carbomer | thickener | 0.1 |
| Sodium hydroxide | neutralizing agent | QS pH 6.5 |
| PURITE ® | preservative | 0.01 |
| Water | hydrophilic vehicle | QS 100 |

Tables 5 and 6 set forth additional non-limiting exemplary formulations contemplated by the practice of the invention.

TABLE 5

| Ingredient | Grade | Formulation A | Formulation B |
|---|---|---|---|
| Testosterone | USP, PhEur | 0.02 | 0.03 |
| Castor oil | USP, PhEur | 0.25 | 0.5 |
| Polyoxyl 40 stearate | NF, PhEur | 0.25 | 0.5 |
| Polysorbate 80 | USP, PhEur | 0.25 | 0.5 |
| Sulfobutyl ether-β-cyclodextrin (Captisol ®) | | 0.25 | 0.3 |
| Glycerin | USP, PhEur | 1.5 | 1.5 |
| Carbomer copolymer type A (Pemulen ™ TR2) | NF | 0.1 | 0.1 |
| Boric acid | NF | 0.6 | 0.6 |
| Sodium hydroxide | USP, PhEur | q.s to pH 7.4 | q.s to pH 7.4 |
| Purified water | USP, PhEur | qs | qs |

TABLE 6

| Ingredient | C % (w/w) | D % (w/w) | E % (w/w) | F % (w/w) | G % (w/w) |
|---|---|---|---|---|---|
| Testosterone | 0.01 | 0.02 | 0.03 | 0.1 | 0.3 |
| Castor oil | 0.25 | 0.25 | 0.25 | 0.25 | 0.25 |
| Polyoxyl 40 stearate | 0.25 | 0.25 | 0.25 | 0.25 | 0.25 |
| Polysorbate 80 | 0.25 | 0.25 | 0.25 | 0.25 | 0.25 |
| Sulfobutyl ether-β-cyclodextrin (Captisol ®) | 0.12 | 0.25 | 0.36 | 1.25 | 3.75 |
| Glycerin | 1.5 | 1.5 | 1.5 | 1.5 | 1.0 |
| Carbomer copolymer type A (Pemulen ™ TR2) | 0.1 | 0.1 | 0.1 | 0.1 | 0.1 |
| Boric acid | 0.6 | 0.6 | 0.6 | 0.6 | 0.6 |
| Sodium hydroxide | Q.S to pH 7.4 | Q.S to pH 7.4 | Q.S to pH 7.4 | Q.S to pH 7.4 | Q.S to pH 7.4 |
| Purified water | Q.S. | Q.S. | Q.S. | Q.S. | Q.S. |

Example 1

Treatment Example

A 50 year old male presents with bilateral redness, inflammation and irritation of the eye. He is diagnosed with blepharitis and treated with the composition disclosed in Table 2. After 3 days of treatment the symptoms are diminished and after 1 week of treatment, the symptoms are eliminated.

Example 2

Alternate Treatment Example

A 55 year old post-menopausal female presents with ongoing irritation, redness and matter accumulation in both eyes. She is diagnosed with blepharitis and treated with the composition disclosed in Table 3. After 2 days she experiences a reduction in irritation and redness and within 1 week experiences a complete cessation of symptoms.

Example 3

Alternate Treatment Example

A 47 year old man is diagnosed with blepharitis. He is treated with the composition disclosed in Table 4 for 2 weeks and experiences an elimination of all symptoms associated with the condition.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

What is claimed:

1. An ophthalmic emulsion comprising testosterone in an amount of about 0.03 w/w % and castor oil in an amount of about 0.25 w/w %, wherein the emulsion is suitable for topical administration to an eye.

2. The emulsion of claim 1, wherein the emulsion further comprises an additional constituent selected from the group consisting of a thickener, neutralizing agent, emulsifier, buffering agent, tonicity agent, demulcent, preservative, plasticizer, occlusive agent, film former, and a combination thereof.

3. The emulsion of claim 1, further comprising an agent selected from the group consisting of an anti-inflammatory, antimicrobial, analgesic, anesthetic, lubricating agent, and a combination thereof.

4. The emulsion of claim 1, further comprising a solubility enhancing agent.

5. A method for treating an ocular condition resulting from an androgen deficiency comprising administering the ophthalmic emulsion of claim 1 to a patient in need thereof, wherein at least one symptom of the ocular condition is alleviated.

6. The method of claim 5, wherein the ocular condition is blepharitis.

7. The method of claim 5, wherein the ophthalmic emulsion comprises an additional constituent selected from the group consisting of a thickener, neutralizing agent, emulsifier, buffering agent, tonicity agent, demulcent, preservative, plasticizer, occlusive agent, film former, and a combination thereof.

8. The method of claim 5, wherein symptoms associated with the ocular condition are reduced.

9. The method of claim 5, wherein symptoms associated with the ocular condition are eliminated.

10. The method of claim 5, wherein the administration is repeated until one or more symptoms of the ocular condition are reduced.

11. The method of claim 5, wherein the administration is repeated until one or more symptoms of the ocular condition are eliminated.

12. The method of claim 5, wherein the ophthalmic emulsion is administered to the eye, upper lid, lower lid, or a combination thereof.

13. An ophthalmic emulsion comprising testosterone in an amount of about 0.1 w/w % and castor oil in an amount of about 0.25 w/w %, wherein the emulsion is suitable for topical administration to an eye.

14. The emulsion of claim 13, wherein the emulsion further comprises an additional constituent selected from the group consisting of a thickener, neutralizing agent, emulsifier, buffering agent, tonicity agent, demulcent, preservative, plasticizer, occlusive agent, film former, and a combination thereof.

15. The emulsion of claim 13, further comprising a solubility enhancing agent.

16. A method for treating an ocular condition resulting from an androgen deficiency comprising administering an ophthalmic emulsion comprising testosterone in an amount of about 0.1 w/w % and castor oil in an amount of about 0.25 w/w % to a patient in need thereof, wherein at least one symptom of the ocular condition is alleviated.

17. The method of claim 16, wherein the ocular condition is blepharitis.

18. The method of claim 16, wherein symptoms associated with the ocular condition are reduced.

19. The method of claim 16, wherein symptoms associated with the ocular condition are eliminated.

20. The method of claim 16, wherein the ophthalmic emulsion is administered to the eye, upper lid, lower lid, or a combination thereof.

21. An ophthalmic emulsion comprising testosterone in an amount of about 0.3 w/w % and castor oil in an amount of about 0.25 w/w %, wherein the emulsion is suitable for topical administration to an eye.

22. The emulsion of claim 21, wherein the emulsion further comprises an additional constituent selected from the group consisting of a thickener, neutralizing agent, emulsifier, buffering agent, tonicity agent, demulcent, preservative, plasticizer, occlusive agent, film former, and a combination thereof.

23. The emulsion of claim 21, further comprising a solubility enhancing agent.

24. A method for treating an ocular condition resulting from an androgen deficiency comprising administering the ophthalmic emulsion of claim 21 to a patient in need thereof, wherein at least one symptom of the ocular condition is alleviated.

25. The method of claim 24, wherein the ocular condition is blepharitis.

26. The method of claim 24, wherein symptoms associated with the ocular condition are reduced.

27. The method of claim 24, wherein symptoms associated with the ocular condition are eliminated.

28. The method of claim 24, wherein the ophthalmic emulsion is administered to the eye, upper lid, lower lid, or a combination thereof.

* * * * *